United States Patent [19]

Jhingan

[11] Patent Number: 5,352,777
[45] Date of Patent: Oct. 4, 1994

[54] DNA ISOLATION FROM ANIMAL CELLS

[75] Inventor: Anil K. Jhingan, Fremont, Calif.

[73] Assignee: Pioneer Hi-Bred International, Inc., Des Moines, Iowa

[21] Appl. No.: 36,208

[22] Filed: Mar. 23, 1993

Related U.S. Application Data

[63] Continuation-in-part of Ser. No. 634,256, Dec. 26, 1990, Pat. No. 5,204,246.

[51] Int. Cl.$^5$ ............................................ C07H 21/00
[52] U.S. Cl. .............................. 536/25.4; 536/25.42; 435/270
[58] Field of Search ...................... 536/25.4–25.42; 435/270

[56] References Cited

U.S. PATENT DOCUMENTS

| | | | |
|---|---|---|---|
| Re. 25,785 | 6/1965 | Beers, Jr. ......................... | 195/29 |
| 3,163,638 | 12/1964 | Miwa et al. ...................... | 260/211.5 |
| 3,582,468 | 6/1971 | Bimbaum et al. ................ | 195/28 |
| 4,830,969 | 5/1989 | Holmes ............................ | 435/259 |
| 4,843,012 | 6/1989 | DeBonville et al. ............ | 435/270 |
| 4,908,318 | 3/1990 | Lemer .............................. | 435/270 |
| 5,047,345 | 9/1991 | DeBonville et al. ............ | 435/270 |
| 5,057,426 | 10/1991 | Henco et al. .................... | 435/270 |
| 5,208,246 | 4/1993 | Jhingan ........................... | 435/270 |

FOREIGN PATENT DOCUMENTS

| | | | |
|---|---|---|---|
| 0127327 | 12/1984 | European Pat. Off. ......... | 536/25.42 |
| 0310913 | 4/1989 | European Pat. Off. ......... | 536/25.42 |

OTHER PUBLICATIONS

Vilee, C. A., et al., The Diversity of Life, *Biology*, Saunders College Publishing; pp. 362–365 (1985).

Pearlmutter, N. L., et al. Localization of Chitin In Algal And Fungal Cell Walls By Light And Electron Microscopy, *The Journal of Histochemistry and Cytochemistry*, vol. 26, No. 10, pp. 782–791 (1978).

Jhingan, "A Novel Technology for DNA Isolation," *Meth. Mol. Cell. Biol.*, vol. 3, pp. 15–22, (1992).

Kreike, "Genetic Analysis of Forest Tree Populations: Isolation of DNA From Spruce and Fir Apices," *Plant Molecular Biology*, vol. 14, pp. 877–879 (1990).

Kamalay et al., "Isolation and Analysis of Genomic DNA from Single Seeds," *Crop Science*, vol. 30, pp. 1079–1084 (1990).

Hempstead et al., "A Method for the Preparation of High-Molecular-Weight DNA from Marine and Freshwater Triclads (Platyhelminthes, Turbellaria)," *DNA and Cell Biology*, vol. 9, No. 1, pp. 57–61 (1990).

Henry et al., "Isolation of High-Molecular-Weight DNA from Insects," *Analytical Biochemistry*, vol. 185, pp. 147–150 (1990).

Couch et al., "Isolation of DNA from Plants High in Polyphenolics," *Plant Molecular Biology Reporter*, vol. 8, No. 1, pp. 8–12 (1990).

Kochiko et al., "A Rapid and Efficient Method for the Isolation of Restrictable Total DNA from Plants of the Genus Abelmoschus," *Plant Molecular Biology Reporter*, vol. 8, No. 1, pp. 3–7 (1990).

Junghans et al., "A Simple and Rapid Method for the Preparation of Total Plant DNA," *Bio Techniques*, vol. 8, No. 2, p. 176 (1990).

(List continued on next page.)

*Primary Examiner*—John W. Rollins
*Assistant Examiner*—L. Eric Crane
*Attorney, Agent, or Firm*—Pioneer Hi-Bred International, Inc.

[57] ABSTRACT

A novel method for the isolation of high molecular weight DNA from plants, yeast bacteria, and animal cells or tissue employs xanthate forming compounds, such as sodium/potassium ethyl xanthogenate. The procedure does not require deproteination and yields clean DNA that is suitable for both PCR and Southern blotting. It can be utilized on a small scale without homogenizing the tissue. These features also facilitate automated screening of tissue samples, one of the labor-intensive techniques in molecular biology.

7 Claims, No Drawings

OTHER PUBLICATIONS

Guidet et al., "A Rapid Method of Preparing Megabase Plant DNA," *Nucleic Acids Research*, vol. 18, No. 16, p. 4955 (1990).

Doyle et al., "Isolation of Plant DNA from Fresh Tissue," *Focus*, vol. 12, No. 1, pp. 13–15 (1990).

Johns et al., "Purification of Human Genomic DNA from Whole Blood Using Sodium Perchlorate in Place of Phenol," *Analytical Biochemistry*, vol. 180, pp. 276–278 (1989).

Mettler I., "A Simple and Rapid Method for Minipreparation of DNA from Tissue Cultured Plant Cells," *Plant Molecular Biology Reporter*, vol. 5, No. 3, pp. 346–349 (Dec. 1987).

Doyle et al., "A Rapid DNA Isolation Procedure for Small Quantities of Fresh Leaf Tissue," *Phytochemical Bulletin*, vol. 19, No. 1, pp. 11–15 (1987).

Hattori et al., "The Isolation of High-Molecular--Weight DNA from Plants," *Analytical Biochemistry*, vol. 165, pp. 70–74 (1987).

Rogers et al., "Extraction of DNA from Milligram Amounts of Fresh, Herbarium and Mummified Plant Tissues," *Plant Molecular Biology*, vol. 5, pp. 69–76 (1985).

Dellaporta et al., "Maize DNA Miniprep." Maize Genetic Cooperation Newsletter, vol. 57, pp. 26–29 (Mar. 1983).

Close et al., "Construction and Characterization of the Chloramphenicol-Resistance Gene Cartridge: A New Approach to the Transcriptional Mapping of Extrachromosomal Elements," *Gene*, vol. 20, pp. 305–316 (1982).

Zimmer et al., "A Simple Method for the Isolation of High Molecular Weight DNA from Individual Maize Seedlings and Tissues," *Maize for Biological Research*, pp. 165–168, Univ. Press, Univ. of N. Dakota (1982).

Rivin et al., "Isolation of DNA and DNA Recombinants from Maize," *Maize for Biological Research*, pp. 161–164, Univ. Press, Univ. of N. Dakota (1982).

Murray et al., "Rapid Isolation of High Molecular Weight Plant DNA," *Nucleic Acids Research*, vol. 8, No. 19, pp. 4321–4325 (1980).

Kislev et al., "Utility of Ethdium Bromide in the Extraction from Whole Plants of High Molecular Weight Maize DNA," *Plant Physiology*, vol. 66, pp. 1140–1143 (1980).

Holl, "DNA Isolation from Plants for Use in DNA Feeding Experiments," *Plant Tissue Culture Methods*, pp. 65–69, (1975).

Howell, "The Isolation and Analysis of DNA from Eukaryotic Cells," *Mol. Tech. Approached Dev. Biol.*, pp. 117–139 (1973).

Guinn, "Extraction of Nucleic Acids from Lyophilized Plant Material," *Plant Physiology*, vol. 41, pp. 689–695 (1966).

Lyttleton et al., "The Isolation of Deoxyribonucleic Acids from Plant Tissues," *Biochem. Biophys. Acta*, vol. 80, pp. 391–398 (1964).

McCormick, "A Solid-Phase Extraction Procedure for DNA Purification," *Analytical Biochemistry*, vol. 181, pp. 66–74 (1989).

Reid, "Organic Chemistry of Bivalent Sulfur," *Thiocarbonic Acids and Derivatives*, vol. 4, Ch. 2, pp. 131–195 (1962).

Donaldson, "Solvent Extraction of Metal Xanthates," *Talenta*, vol. 23, pp. 417–426 (1976).

DNA ISOLATION FROM ANIMAL CELLS

The present application is a continuation-in-part application of U.S. Ser. No. 07/634,256, filed Dec. 26, 1990, now U.S. Pat. No. 5,204,246, Apr. 20, 1993.

TECHNICAL FIELD

This invention relates to the isolation of DNA from whole plants and plant cells, tissues and parts, from yeasts and bacteria, and from animal cells and tissues.

BACKGROUND OF THE INVENTION

With the increasing need for DNA fingerprinting, restriction fragment length polymorphism (RFLP) analysis, Southern transfers, construction of genomic libraries and transformation experiments in biotechnology, the isolation of high molecular weight (HMW) DNA becomes a major problem. Several procedures for the isolation of HMW DNA have been reported, all of which have drawbacks for various reasons. The methods generally involve physical grinding of cells or tissue followed by extraction in buffers containing detergent, EDTA, Tris and other reagents. Some of the reagents used react with various cellular organelles; the function of others is unknown.

The prior art methods are often time consuming, irreproducible and give variable yields of DNA, involving more art than science. The DNA obtained also varies in terms of its purity, and all of the methods involve purification of DNA with phenol, a protein denaturant which can be hazardous to users. Finally, a method that is effective in DNA extraction in one plant or animal group often fails when used on other plants or animals.

More recently, a solid phase extraction material comprising silica and having hydroxyl groups on its surface has been reported as a replacement for phenol for removal of proteins. However, the preparation of this material is cumbersome, and grinding of tissue is still needed.

In view of these difficulties, a continuing need exists for a versatile method that would overcome these problems.

It is an object of this invention to provide such a method.

DISCLOSURE OF THE INVENTION

While not intending to be limited by theory, the isolation of DNA from plants, yeasts and bacteria is difficult partly due to the presence of a rigid cell wall which is rich in polysaccharides and therefore difficult to rupture completely with commonly used buffers. Removal of the cell wall by enzymes is tedious and not always feasible. Variations in DNA yield and quality from extraction to extraction using current methods probably arises from the varying degrees of cell wall break up. Thus, there has been a need for new technique for disrupting cell walls by a thorough, yet delimited mechanism to allow isolation of DNA in a reproducible manner without the need to homogenize cells or tissues.

Polyhydric alcohols, including cellulose, have been solubilized in the past by conversion to metal xanthates. This method was discovered by Zeise in 1815 and it has been widely employed in the textile industry. Xanthates find extensive application in the separation and quantitative determination of numerous metal ions by taking advantage of the low and differential solubilities of metal xanthates under controlled pH conditions.

It has now been determined that the replacement of existing reagents for DNA extraction by xanthate-forming compounds is feasible and highly advantageous. It was postulated that these compounds would dissolve the cell wall in plants by forming water soluble polysaccharide xanthates with the hydroxyl groups of polysaccharides which make up a substantial portion of plant cell walls. The reaction of xanthate-forming compounds with amines is also reported. Furthermore, xanthate-forming compounds can also bind metal ions to inhibit DNAase activity. As a result, these compounds enable selectively dissolving DNA from cell organelles, leaving contaminating proteins, metal ions and other compounds as an insoluble residue. DNA can then be precipitated from the supernatant.

The same xanthate-forming compounds can be effectively used for the efficient extraction of DNA from animal cells and tissues. The isolated DNA is free of contaminants that interfere with restriction enzyme digestion.

Xanthate-forming compounds

The "xanthate-forming compounds" of this invention include any compound capable of forming xanthate reaction products with cell wall polysaccharides from plant cells. These specifically include carbon disulfide and its organoalkaline derivatives. While the common reagent used in industrial use of this reaction (the viscose rayon process) is carbon disulfide, for analytical isolation of DNA according to this invention the organoalkaline derivatives of carbon disulfide are preferred. By "organoalkaline derivatives of carbon disulfide" is meant compounds of the general formula

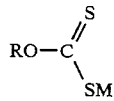

wherein R is an unsubstituted or substituted alkyl, alkenyl or aralkyl group, preferably selected from methyl, ethyl, propyl, butyl, hexyl, isoamyl, vinyl, allyl, 2-3-dihydroxypropyl, phenethyl, 4-morpholinylmethyl, and hydroxyphenethyl; and wherein M is an alkali metal or $NH_4$, preferably Na or K. These compounds are formed by reaction of carbon disulfide with the corresponding alcoholic alkali:

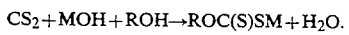

The most preferred of these compounds, the carbonodithioic acid o-ethyl ester, sodium salt ($R=C_2H_5$, $M=Na$; sodium ethyl xanthogenate) can be prepared by standard methods, and its potassium analogue is commercially available from Fluka. The entire class of compounds useful in this invention (including carbon disulfide) can thus be represented by the formula

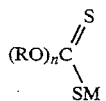

wherein n is 0 or 1; R is an unsubstituted or substituted alkyl, alkenyl or aralkyl group, preferably selected from methyl, ethyl, propyl, butyl, hexyl, isoamyl, vinyl, allyl, 2-3-dihydroxypropyl, phenethyl, 4-morpholinylmethyl, and hydroxyphenethyl; and wherein M is alkali metal or ammonium, preferably Na or K, when n is 1 and another bond to the carbon when n is 0.

The methods described herein using these compounds enable efficient DNA isolation without homogenizing tissues and without removing proteins.

EXAMPLE I

Tissue Grinding Protocol

Fresh leaf material (0.6–0.63 g) of thirteen day old corn seedlings was frozen in a liquid nitrogen bath until it was very brittle and was ground to a fine powder using a glass homogenizer. The powder was suspended in 4 ml buffered extraction reagent (694 mM carbonodithioic acid, o-ethyl ester, sodium salt, 100 mM Tris, pH 7.5, 700 mM NaCl 10 mM EDTA, pH 8 or 625 mM carbonodithioic acid, o-ethyl ester, potassium salt, 100 mM Tris, pH 7.5, 700 mM NaCl, 10 mM EDTA) in 15 ml propylene tube. After 5 min. incubation at 65°, the leaf debris was removed by filtering the homogenate through Miracloth. The DNA was precipitated from the filtrate by addition of two volumes of ethanol and centrifuged for 10 minutes at 3K at 4°.

The pellet was suspended in 100 μl TE and centrifuged for 3 min. as before to remove precipitated proteins and metal xanthates. The supernatant was transferred into 1.5 ml Eppendorf tube and centrifuged for 5 minutes. The DNA was precipitated again from the supernatant by adjusting to 2M NH4OAC and adding two volumes of ethanol. DNA was pelleted by centrifuging for 5 min. at 735 g. After decanting the supernatant, the pellet was dried in a speed vac and redissolved in 100 μl TE buffer. The yield of DNA was 20–40 μg.

EXAMPLE II

Non-Grinding Protocol 1 g of fresh leaves in 4 ml of extraction buffer containing carbonodithioic acid, o-ethyl ester, sodium salt are incubated at 65° for 20 min. and filtered. The DNA is precipitated from the filtrate and reprecipitated as above. This non-grinding method applied to corn yielded 2.56 to 6.68 μg DNA per gram of leaf tissue.

EXAMPLE III

To evaluate the protocols of Examples I and II, DNA isolated was digested for 6 h with Bam HI and Hind III, EcoRI and Sst I and assayed by agarose gel electrophoresis. The undigested DNA showed an apparent molecular weight greater than the λ marker which is 23 kb. The absence of high molecular weight DNA and presence of smear in the digested samples suggested that DNA was completely digested and was free of contaminants which interfere with restriction enzyme digestion.

EXAMPLE IV

The quality of the DNA preparations was further assessed by Southern transfer experiments. Isolated DNA was digested with Bam HI, electrophoresed, transferred to MSI membrane and hybridized with 32p single copy probes.

Undigested and digested DNA gave the expected hybridization pattern. The appearance of discrete bands in the digested samples confirmed that the DNA was digested completely by the enzyme and that the hybridization with the probe was successful. This is an important criterion for the quality of DNA.

EXAMPLE V

To further substantiate the quality of the isolated DNA for molecular biology applications, extracted DNA was assayed by polymerase chain reaction (PCR). After isolation, the DNA was amplified and the products were run on an agarose gel. A control experiment was also performed in which template DNA was not included in the PCR reaction. The absence of the expected target band in the control and its presence in the DNA samples obtained from the foregoing protocols further confirmed the quality of DNA.

EXAMPLE VI

The yield and efficiency of these extraction procedures was tested with a grinding protocol. Addition of a known amount (20 μg) of DNA to the leaf sample prior to homogenization and following the same steps yielded at least 81% DNA in the final step. This suggested that losses of DNA due to enzymatic or mechanical degradation were minimum.

EXAMPLE VII–XII

The grinding method has also been successfully employed for the isolation of DNA from thirteen-day-old seedlings of soybean, sorghum, sunflower, alfalfa and tobacco as determined by agarose gel electrophoresis and Southern transfers. Results are shown in Table 1.

TABLE 1

| Ex. | Plant | Yield[1] | High DNA Quality[2] | Southern Blot |
|---|---|---|---|---|
| VI | Alfalfa | 15–42 | Yes | works |
| VIII | Canola | 8–14 | Yes | |
| IX | Sorghum | 12–28 | Yes | works |
| X | Soybean | 26–37 | Yes | works |
| XI | Sunflower | 7–30 | Yes | |
| XII | Tobacco | 7–30 | Yes | |

[1] μg/600–630 mg fresh leaves
[2] DNA is completely digested by Bam HI

EXAMPLE XIII–XXIV

The versatility of these two methods (grinding and nongrinding) was also compared on alfalfa, barley, canola, sorghum, soybean, sunflower, tobacco, wheat, petunia, spinach, yeast and E. coli. With yeast and E. coli, homogenization was omitted in the grinding protocol. Table 2 gives the yields of DNA.

TABLE 2

| Ex. | Plant | Yield[1] grinding method | Yield[2] non-grinding method |
|---|---|---|---|
| XIII | Alfalfa | 15–42 | 1.50–2.80 |
| XIV | Canola | 8–14 | 2.70–4.80 |
| XV | Sorghum | 12–28 | 1.70–2.66 |
| XVI | Soybean | 26–37 | 0.45–1.14 |
| XVII | Sunflower | 7–30 | 0.13–1.34 |
| XVIII | Tobacco | 7–30 | 1.00–3.74 |
| XIX | Petunia | 11–19 | 2.07–2.27 |
| XX | Lettuce | 18–43 | 1.63–2.17[3] |
| XXI | Wheat | 7–38 | 1.12–4.27 |
| XXII | E. coli | 50 | 22–25 |
| Different Series: | | | |
| XXIII | Spinach | 20.64 | 1.4346 |
| XXIV | Yeast | 1.239 | 2.369 |

[1] μg/600–630 mg fresh tissue
[2] μg DNA/1 g fresh tissue
[3] μg DNA/2 g (market-purchased) lettuce

EXAMPLE XXV–XXVI

The method of this invention was also applied successfully for the isolation of DNA from the following plants:

| Ex. | Plant |
|---|---|
| XXV | Celosia |
| XXVI | Alyssum |

The simplicity of the non-grinding method may facilitate automation of DNA isolation and field use of analytical and diagnostic methods requiring DNA isolation by non-specialists. The wide applicability of the grinding method of this invention makes it a potential general method of DNA isolation from plant cells. The extractions have been attempted at various temperatures using different concentrations of substrates under various pH values, using different amounts and concentrations of buffer.

With the non-grinding method, alfalfa, corn, sorghum and lettuce gave high yield and quality of DNA using 2 ml of buffer/reagent. On the other hand, isolation of DNA from soybean, sunflower and wheat using sodium ethyl xanthogenate required twice that amount to give clean DNA. With canola, tobacco and petunia, slight gentle homogenization prior to incubation helped to give better quality and yield of DNA. Thus, it can be seen that numerous specific embodiments of the methods of this invention can be optimized to suit the specific in vivo or in vitro system under consideration.

EXAMPLE XXVII–XXVIII

The method of this invention was also applied successfully for the isolation of DNA from animal tissue. Approximately 1.0 g samples of drained chicken liver were ground unfrozen with a mortar and pestle. Approximately 5 ml of fresh buffered extraction reagent (624 mM potassium ethyl xanthogenate; 100mM Tris, pH 7.5, 700 mM NaCl; 10 mM EDTA) was added to the mortar. The mixture was ground until a reasonably smooth slurry was obtained. The slurry was poured into a sterile 15 ml polypropylene tube and incubated at 65° C. for 15 minutes. The tubes were cooled to room temperature and then spun at 14,460 g for 15 minutes.

The supernatants in each tube were precipitated with equal volumes of cold isopropanol in new polypropylene tubes. The tubes were incubated at −20° C. for 15 min. The pink pellets were rinsed with ethanol, dried at room temperature and resuspended in 300 μl sterile distilled water.

The yield of DNA from 1.0 g samples of liver tissue using the method of the present invention was 150 to 159 ηg. In contrast, the yield of DNA from 1.0 g samples of the same liver tissue extracted using the well known CTAB method, as taught by Saghai-Maroof et al., PNAS 81: 8014–8018 (1984) which is herein incorporated by reference, was 74 to 88 ηg.

The method of this invention was also applied to EDTA-treated rabbit blood obtained from Bethel Laboratories. Approximately 10 ml samples of blood were each placed in 15 ml polypropylene tubes and centrifuged at 14,460 g for 20 minutes. The cell pellets were not ground or vortexed. The pellets were drained and resuspended in 3 ml of buffered extraction reagent (624 mM potassium ethyl xanthogenate; 100mM Tris, pH 7.5, 700 mM NaCl 10 mM EDTA). The tubes were incubated at 65° C. for 15 minutes and then cooled to room temperature. The remaining steps in the DNA isolation method were the same as that described above for liver tissue, except that the final DNA pellet was resuspended in 100 μl of sterile distilled water.

The yield of DNA from 10 ml samples of blood using the method of the present invention was 28 to 30 ηg. In contrast, the yield of DNA from 10 ml of the same blood extracted using the CTAB method was 24 to 27 ηg.

To evaluate and compare DNA isolated from liver tissue and rabbit blood using the method of the instant invention and the CTAB method, DNA samples were digested overnight with EcoRl and assayed by agarose gel electrophoresis. Both the undigested control DNA samples and the digested DNA samples, produced by either the CTAB method or the method of the instant invention, appeared equivalent. Both produced a smear suggesting the DNA was completely digested and was free of contaminants that interfere with restriction enzyme digestion.

What is claimed is:

1. A method for isolating DNA from animal cells or tissues, comprising the steps of contacting said cells or tissue with an aqueous solution comprising a compound or compounds that are xanthate-forming compounds, and isolating DNA from the cells.

2. A method according to claim 1 wherein said compound or compounds has the formula

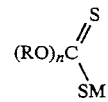

wherein n is 0 or 1; R is unsubstituted or substituted lower alkyl, lower alkenyl, or aralkyl; and M is alkali metal or ammonium when n is 1 and a sulfur-carbon bond when n is 0.

3. A method according to claim 2 wherein n is 1, R is unsubstituted or substituted lower alkyl, and M is Na or K.

4. A method according to claim 3 wherein R is selected from the group consisting of methyl, ethyl, propyl, butyl, hexyl, isoamyl, and 2-3-dihydroxypropyl.

5. A method according to claim 4 wherein the compound or compounds is the sodium or potassium salt of ethyl xanthogenate.

6. A method according to claim 1, further comprising the step of removing cellular debris from the solution by means of centrifugation.

7. A method according to claim 6, further comprising the step of precipitating the DNA from the centrifuged solution with ethanol.

* * * * *